United States Patent [19]

Nanaumi

[11] Patent Number: 4,932,394
[45] Date of Patent: Jun. 12, 1990

[54] ENDOSCOPE INCLUDING SCOPE TERMINAL LOCKING INDICATOR

[75] Inventor: Yasuaki Nanaumi, Tochigi, Japan

[73] Assignee: Kabushiki Kaisha Toshiba, Kawasaki, Japan

[21] Appl. No.: 230,386

[22] Filed: Aug. 10, 1988

[30] Foreign Application Priority Data

Aug. 10, 1987 [JP] Japan .................. 62-198337

[51] Int. Cl.<sup>5</sup> .............................. A61B 1/00
[52] U.S. Cl. ................................... 128/4
[58] Field of Search ................. 128/4, 6; 358/98

[56] References Cited

U.S. PATENT DOCUMENTS 4,617,914  10/1986  Ueda .............................. 128/4
4,714,075  12/1987  Krauter et al. ................. 128/4

Primary Examiner—William H. Grieb
Attorney, Agent, or Firm—Foley & Lardner, Schwartz, Jeffery, Schwaab, Mack, Blumenthal & Evans

[57] ABSTRACT

An endoscope including a scope having a terminal portion with an optoelectronic device such as a CCD for observing an object to pick up picture signals, and a processor for operating picture signals, in which the terminal portion is locked at a certain bending angle by a locking device, and the locking of the terminal portion is indicated in sound, light and a picture by a locking indicator such as a lamp, a flasher, a LED, a speaker, a buzzer, a display and the like.

8 Claims, 3 Drawing Sheets

ENDOSCOPE INCLUDING SCOPE TERMINAL LOCKING INDICATOR

BACKGROUND OF THE INVENTION

1. Field of the Invention

This invention relates to an endoscope and, more particularly, to an endoscope including an indicator such as a lamp, a flasher, a buzzer, a speaker, a display and the like for indicating a locking state of a terminal portion of a scope.

2. Description of the Prior Art

In general, as well known, a conventional endoscope includes a scope to be inserted into the inside of an internal organ such as the stomach and the like, a vertical angle adjusting knob for adjusting a bending angle of a hard terminal portion of the scope in the vertical direction, and a horizontal angle adjusting knob for adjusting the bending angle of the hard terminal portion of the scope in the horizontal direction. When the terminal portion of the scope is temporarily locked at the desired bending angle, a pair of locking devices attached to the respective vertical and horizontal angle adjusting knobs are operated. However, even when the vertical and horizontal locking devices are operated to lock the terminal portion of the scope, usually, the vertical and horizontal angle adjusting knobs can be freely turned in a manual operation to change the bending angle of the terminal portion of the scope. If the locked terminal portion of the scope is carelessly moved during an operation using the endoscope, a subject may readily suffer damage, which is very dangerous for the subject, and thus an operator must memorize whether the terminal portion of the scope is locked or not.

However, the conventional endoscope is not provided with such an indicator for indicating the locked state of the terminal portion of the scope, and the operator is required to consciously and clearly memorize whether the hard terminal portion of the scope is locked or not. When the operator's memory of the locking state of the terminal portion becomes uncertain during the operation of the endoscope, he will move his eye to the locking devices in order to confirm whether the locking devices are operated or not. Further, when the locking state of the terminal portion of the scope is confirmed by eye, if locking positions of locking levers of the locking devices are not clearly memorized, a misunderstanding or a mistake is liable to happen in judging whether the locking devices are functioned or not, which is also dangerous and inconvenient.

SUMMARY OF THE INVENTION

Accordingly, it is an object of the present invention to provide an endoscope including means for indicating a locking state of a terminal portion of a scope to an operator, free from the aforementioned inconveniences and defects of the prior art, which helps an operator to know readily and clearly the locking state of the terminal portion of the scope, and which is simple in its construction.

In accordance with one aspect of the present invention, there is provided an endoscope comprising a scope having a terminal portion, for observing an object to pick up picture signals, means for processing the picture signals picked up by the scope, means for locking the terminal portion at a certain bending angle, means for indicating a locking of the terminal portion of the scope.

BRIEF DESCRIPTION OF THE DRAWINGS

The above and other objects, features and advantages of the present invention will more fully appear from the following description of the preferred embodiments with reference to the accompanying drawings, in which.

DETAILED DESCRIPTION OF THE PREFERRED EMBODIMENTS

The present invention will now be described in detail with reference to its preferred embodiments in connection with the accompanying drawings.

Figure 1:
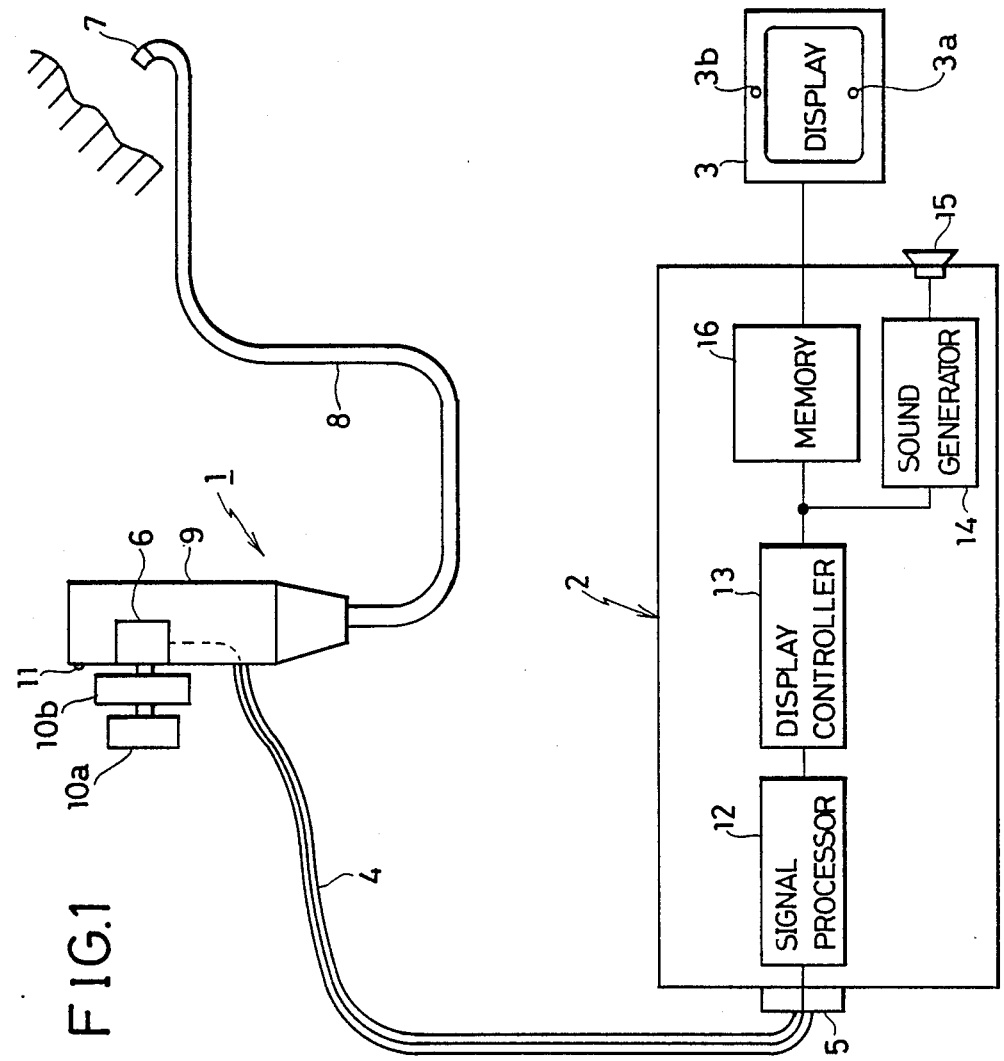
FIG. 1 is a block diagram of one embodiment of an endoscope including an indicator for indicating a locking state of a terminal portion of a scope according to the present invention.

In FIG. 1, there is shown one embodiment of an endoscope according to the present invention. The endoscope comprises a scope 1 for observing an inside of an internal organ such as the stomach or the intestines to pick up picture signals of an object, a system body 2 for processing the picture signals picked up by the scope 1, and a display 3 such as a CRT for monitoring a picture thereon. The scope 1 and the system body 2 are connected to each other through a cable 4 and a connector 5 attached to the system body 2.

The scope 1 includes a detector portion 6 for detecting a locked state of a hard terminal portion 7, a flexible longitudinal guide portion 8 and an operating portion 9. The terminal portion 7 of the scope 1 is formed at the terminal of the guide portion 8 and includes an opto-electronic device such as a charge coupled device (CCD) for photographing the object. The terminal portion 7 is bent freely at a desired angle by vertical and horizontal angle adjusting knobs 10a and 10b pivotally mounted on the operating portion 9. The horizontal angle adjusting knob 10a adjusts the bending angle of the hard terminal portion 7 in the horizontal direction, and the vertical angle adjusting knob 10b adjusts the bending angle of the hard terminal portion 7 in the vertical direction.

The operating portion 9 is provided with an indicator lamp 11 on its upper portion for indicating the locking state of the terminal portion 7 of the scope 1. A flasher lamp or a LED may be provided instead of the lamp 11.

The system body 2 includes a signal processor 12 for converting the picture signals picked up by the CCD into video signals and for conducting an analog-digital (A/D) conversion of the video signals, a display controller 13 for controlling the display 3, a sound generator 14 for generating a sound signal to a loudness speaker 15 connected thereto, and a picture memory 16 for storing the picture signals fed from the display controller 13. The picture signals are read out of the picture memory 16 to display the picture on the display 3. In this case, a buzzer may be used instead of the speaker 15.

The display 3 includes a flasher point portion or marker portion 3a for indicating the locking state of the terminal portion 7 of the scope 1 in a proper portion of the display surface, for example, the lower central portion, and a flasher lamp 3b also for indicating the locking state of the terminal portion 7 of the scope 1 may be arranged on a frame of the display 3 in the upper central portion. A LED may be provided instead of the flasher lamp 3b.

Figure 2:
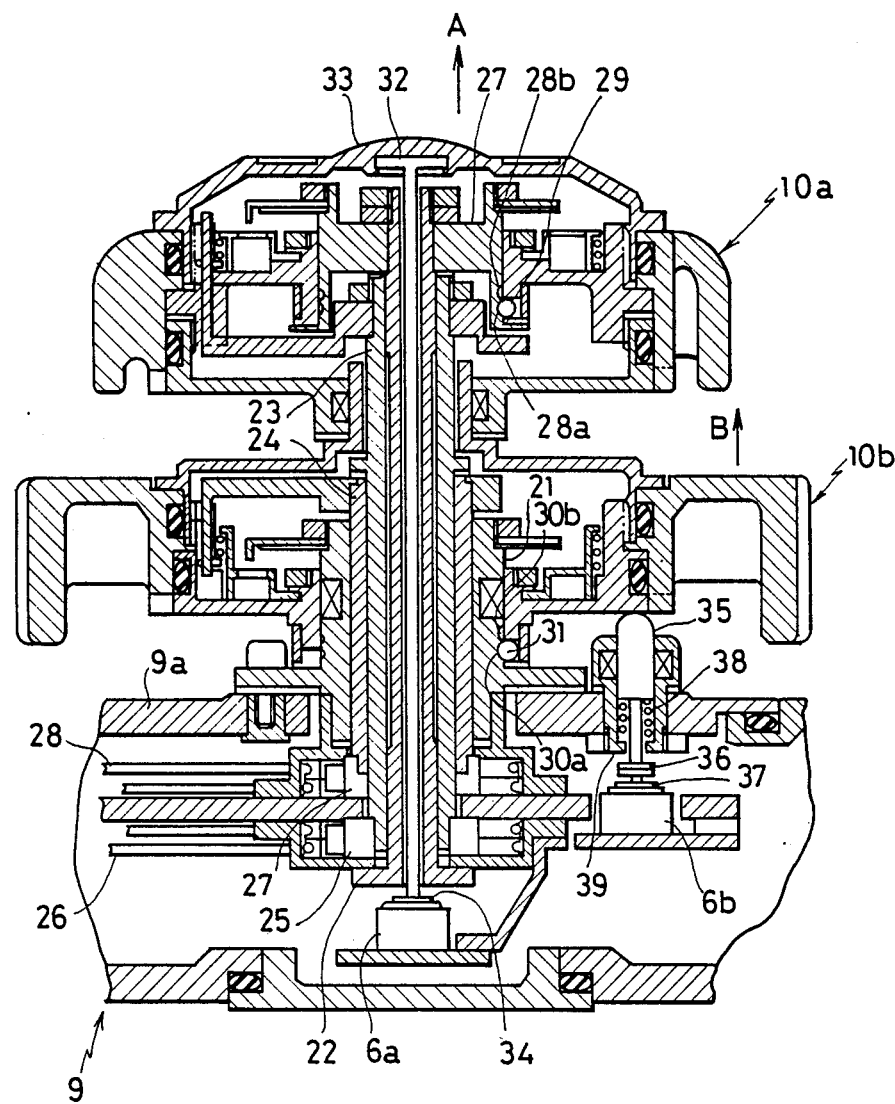
FIG. 2 is a longitudinal cross sectional view of vertical and horizontal angle adjusting knobs of the endoscope illustrated in FIG. 1.

In FIG. 2, there is shown one embodiment of the essential part of the operating portion 9 having a case body 9a, which includes the horizontal angle adjusting knob 10a, the vertical angle adjusting knob 10b, and the detector portion 6 having a pair of micro switches 6a and 6b for detecting locking operations of respective locking devices 25 and 27 described hereinafter in detail.

A fixed tubular shaft 21 is secured to the body case 9a of the operating portion 9, and another fixed tubular shaft 22 penetrating the shaft 21 is mounted to the body case 9a through inner and outer tubular sleeves 23 and 24. These members 21, 22, 23 and 24 are coaxially arranged. The inner and outer tubular sleeves 23 and 24 are slidably and rotatably arranged between the tubular shafts 21 and 22.

The sleeves 23 and 24 are fixedly connected to the horizontal and vertical angle adjusting knobs 10a and 10b, respectively. By rotating the horizontal angle adjusting knob 10a together with the sleeve 23, the horizontal angle of the terminal portion 7 is adjusted through a locking device 25 and a wire 26. By rotating the vertical angle adjusting knob 10b along with the sleeve 24, the vertical angle of the terminal portion 7 is adjusted through a locking device 27 and a wire 28.

Then, when the horizontal and vertical angle adjusting knobs 10a and 10b are pulled up in the directions indicated by arrows A and B in FIG. 2, the sleeves 23 and 24 are pulled up and the locking devices 25 and 27 lock the movement of the wire 26 and 28 and thus the bending angle of the terminal portion 7 of the scope 1. In this embodiment, as mentioned above, the horizontal and vertical angle adjusting knobs 10a and 10b can be freely rotated in a manual operation to change the bending angle of the terminal portion 7 of the scope 1, even when the locking devices 25 and 27 are operated.

A fixed shaft 27 is screwed to the shaft 22 on its upper end portion A pair of channels, i.e., lower and upper ones 28a and 28b are caved on the lower and outer periphery of the fixed shaft 27. A click ball 29 is fitted into the lower channel 28a as long as the horizontal and vertical angle adjusting knobs 10a and 10b are not pulled up, while the horizontal angle adjusting knob 10a can be rotated freely around the shaft 27.

A pair of channels, i.e., lower and upper ones 30a and 30b are formed on the lower and outer periphery of the shaft 2. A click ball 31 is fitted into the lower channel 30a as long as the horizontal and vertical angle adjusting knobs 10a and 10b are not pulled up, while the vertical angle adjusting knob 10b can be rotated freely around the shaft 21.

A movable rod 32 vertically extends through an axial opening of the shaft 22. The top of the rod 32 is mounted to a cover 33 attached to the horizontal angle adjusting knob 10a, and the lower end of the rod 32 contacts a detecting surface 34 of the micro switch 6a arranged near the lower end of the shaft 22 when the horizontal and vertical angle adjusting knobs 10a and 10b are not pulled up.

Another movable rod 35 having a stopper 36 on its lower end portion is movably mounted to the body case 9a of the operating portion 9. When the horizontal and vertical angle adjusting knobs 10a and 10b are not pulled up, the upper end of the rod 35 contacts the vertical angle adjusting knob 10b and the lower end of the rod 35 contacts a detecting surface 37 of the micro switch 6b mounted to the body case 9a. The rod 35 is biased upwards by a spring 38, and thus the rod 35 is movable upwards until the stopper 36 contacts a guide surface 39.

The operation of the abovementioned endoscope of the present embodiment will now be described.

In the drawings, the terminal portion 7 of the scope 1 is inserted into the inside of the internal organ or the like, and the terminal portion 7 is suitably controlled to be bent for observing the object by operating the horizontal and vertical angle adjusting knobs 10a and 10b.

Now, in order to lock the terminal portion 7 of the scope 1, the locking devices 25 and 27 are operated by pulling up the horizontal and vertical angle adjusting knobs 10a and 10b as indicated by the arrows A and B in FIG. 2. Then, the click balls 29 and 31 are moved from the lower channels 28a and 30a to the upper channels 28b and 30b, respectively, to hold the horizontal and vertical angle adjusting knobs 10a and 10b in their upper locking positions.

In the same time, the rods 32 and 35 are moved upwards, and the lower end of the rod 32 and the stopper 36 of the rod are separated from the detecting surfaces 34 and 37 of the micro switches 6a and 6b, respectively. Thus, the micro switches 6a and 6b detect the locking operations of the locking devices 25 and 27 or the locking state of the terminal portion 7 of the scope 1, and output electric signals to the signal processor 12 of the system body 2 through the cable 4.

In the system body 2, the signal processor 12 sends the signals to the display controller 13, and the display controller 13 outputs control signals for indicating the locking state of the terminal portion 7 of the scope 1 to the sound generator 14 and the display 3 via the memory 16. Then, the sound generator 14 drives the speaker 15 to generate indication sound such as intermittent sound or the like, and/or the display 3 displays the locking state thereon by flashing the flasher point portion 3a and the flasher lamp 3b or by illustrating a character or symbol for the locking state in a proper portion on the display 3. The indicator lamp 11 is also illuminated according to the electric signals output by the micro switches 6a and 6b, in the same time.

As described above, the endoscope of the present embodiment is constructed so that various kinds of indications, for instance, using sound, light and a picture may be made when the terminal portion 7 of the scope 1 is locked in a certain shape in order to easily and clearly indicate the locking of the terminal portion 7 to the operator. Accordingly, a danger and a damage due to a careless accident by the operator can be effectively prevented.

Figure 3:
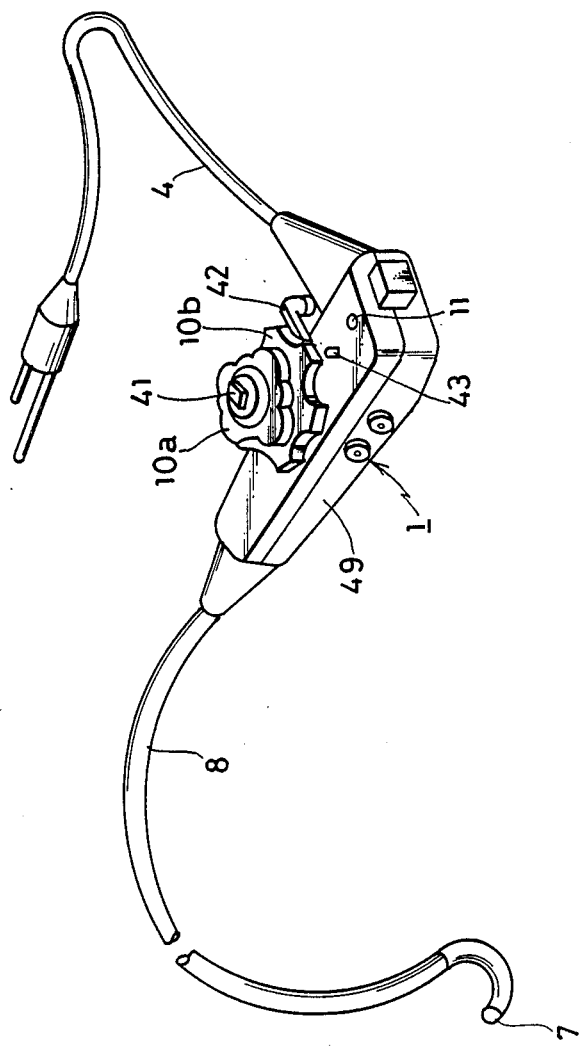
FIG. 3 is a perspective view of another embodiment of an endoscope according to the present invention.

In FIG. 3, there is shown a second embodiment of the scope 1 of the endoscope according to the present invention, wherein like members to those of the first embodiment have the same functions and thus the description of the like members may be omitted.

In this embodiment, the endoscope has the same construction as the first embodiment, except that an operating portion 49 includes a pair of locking levers 41 and 42 for functioning locking devices which can lock the horizontal and vertical bending angles of the terminal portion 7 of the scope 1, by turning the locking levers approximately 90 degrees in a clockwise direction.

For example, when the locking levers 41 and 42 are turned in the clockwise direction from the position shown in FIG. 3, where the locking devices are not actuated, the locking levers 42 contacts a micro switch 43 for detecting the locking operation of the locking device which locks the vertical bending angle of the terminal portion 7, and the micro switch 43 outputs an electric signal to the system body 2 through the cable 4 in the same manner as the first embodiment. Another micro switch (not shown) is provided for the locking lever 41.

In this embodiment, when the micro switches detect the locking operations of the locking devices, the locking state of the terminal portion 7 of the scope 1 is indicated to the operator in the same manner as the first embodiment described above, resulting in the same effects and advantages as those of the first embodiment.

Although the present invention has been described in its preferred embodiments with reference to the accompanying drawings, it is readily understood that the present invention is not restricted to the preferred embodiments and that various changes and modifications may be made in the present invention by a person skilled in the art without departing from the spirit and scope of the present invention.

I claim:

1. An endoscope, comprising:
    a scope having a terminal portion, for observing an object and picking up picture signals therefrom;
    means for processing the picture signals picked up by the scope;
    means for locking the terminal portion at a certain bending angle;
    means for indicating the locking of the terminal portion of the scope; and
    means for detecting the locking of the terminal portion to output a locking signal to the indicating means.

2. The endoscope of claim 1, wherein the indicating means includes a speaker.

3. The endoscope of claim 1, wherein the indicating means includes a buzzer.

4. The endoscope of claim 1, wherein the indicating means includes a lamp.

5. The endoscope of claim 1, wherein the indicating means includes a flasher.

6. The endoscope of claim 1, wherein the indicating means includes a LED.

7. The endoscope of claim 1, wherein the indicating means includes a display.

8. The endoscope of claim 1, wherein the detecting means includes switches for detecting the locking of horizontal and vertical bending angles of the terminal portion locked by horizontal and vertical locking devices.

* * * * *